(12) United States Patent
Matulevich

(10) Patent No.: US 6,764,656 B1
(45) Date of Patent: Jul. 20, 2004

(54) AIR FRESHENER SPORTS FIGURE FAN FOR AIR VENTS

(76) Inventor: Jeffrey B. Matulevich, 68 Arbor Oaks Dr., Sarasota, FL (US) 34232

( * ) Notice: Subject to any disclaimer, the term of this patent is extended or adjusted under 35 U.S.C. 154(b) by 0 days.

(21) Appl. No.: 10/443,333

(22) Filed: May 22, 2003

(51) Int. Cl.$^7$ ................................................. A62B 7/08
(52) U.S. Cl. ........................ 422/124; D23/367; 454/157; 446/124
(58) Field of Search ........................ 454/157; D23/324, D23/367; 40/421, 422; 422/123, 124; 446/199, 201; 239/34, 53, 55, 56, 57

(56) References Cited

U.S. PATENT DOCUMENTS

| | | | |
|---|---|---|---|
| 1,675,141 A | * | 6/1928 | Scholl .......................... 40/422 |
| 2,545,801 A | * | 3/1951 | Wrazen ........................ 40/412 |
| 2,573,625 A | * | 10/1951 | Swart ........................... 40/422 |
| D196,639 S | | 10/1963 | Irving |
| D275,784 S | | 10/1984 | Reedman |
| 4,546,562 A | * | 10/1985 | Jones ........................... 40/591 |
| D287,049 S | | 12/1986 | Torres |
| 4,840,773 A | * | 6/1989 | Wade .......................... 422/124 |
| 5,593,641 A | | 1/1997 | Hornberger, Sr. |
| 5,816,951 A | | 10/1998 | Hudock |
| 5,876,678 A | | 3/1999 | Harrell et al. |
| D429,325 S | | 8/2000 | Macaree |
| 6,103,201 A | * | 8/2000 | Green .......................... 422/124 |
| D433,745 S | | 11/2000 | Cowell |
| D434,260 S | | 11/2000 | Rosenstadt et al. |
| 6,161,820 A | * | 12/2000 | Wu ............................. 261/104 |
| 6,270,720 B1 | | 8/2001 | Mandish |

* cited by examiner

*Primary Examiner*—Harold Joyce
(74) *Attorney, Agent, or Firm*—Dennis G. LaPointe; Mason Law, P.L.

(57) ABSTRACT

A sports figure shaped fan for ventilation grills comprising a caricature formed in the shape of a sports figure. The sports figure shaped fan is attached to a ventilation grill and the arms are extended and rotate when subjected to a back draft from the air flow of the ventilation system. The rotation mimics a throwing action of the sports figure. The sports figure shaped fan also includes a reservoir and access to the reservoir for inserting one of a scenting agent, a deodorizing agent and a combination thereof, in the reservoir located in a designated portion of the caricature. The designated portion of the sports figure caricature is sufficiently permeable on either side of the reservoir so that when the air flow passes by the sports figure, a vapor is dispersed by the movement of the air flow emanating from the ventilation grill.

14 Claims, 5 Drawing Sheets

AIR FRESHENER SPORTS FIGURE FAN FOR AIR VENTS

The invention relates to a fan for an air vent such as in the dashboard of an automobile that is formed in the shape of a sports figure and whose arms rotate to serve as fan blades with the device being capable of dispersing an aromatic scent for freshening an area, such as the personnel compartment of the vehicle.

There are air fresheners or deodorizers for automobiles that are formed in the shaped for various action figures such as the deodorizer disclosed in Design Pat. No. 196,639 to Irving, which hangs from any part of the interior compartment of a vehicle, Another air freshener is that disclosed in Design Pat. No. 287,049 to Torres, which is simply a thin card that hangs from any part of the interior compartment of a vehicle.

The Torres patent does disclosed an imprint of a soccer player but there is no action associated with the sports figure. Similarly, there is no action associated with the caricature depicted in the Irving patent. As such, it simply hangs in the vehicle in a non-noticeable non-entertaining fashion.

The present invention provides the benefits of devices such as those mentioned above, in addition, to providing a fan like effect with the rotating arms that mimic a throwing action of a sports figure, such as a baseball player, a basketball player, a football player, and other sport caricatures that have a throwing action as part of the sport game.

Aromatic/deodorizing scents can be optionally incorporated into the device by addition of aromatic or deodorizing agents such as beads, wax or oil in absorbent material in a designated portion of the device, preferably the head portion of the device. Should the head portion be designated to contain the scent/deodorizing means, then access means to a small holding area or reservoir could be through a slot at the top of the head, the face, a face visor, a face guard, a face mask, or the cap/helmet portion of the head. It is preferable that scenting means be something other than oils, although oils in an absorbent material would work. Preferably means such as beads or scented wax would be longer lasting and easier to market and use with the device. For example, if the sports figure is a football player, the helmet portion may be integral to the body portion but the visor or face mask may be removable to insert the aromatic/deodorizing pellets (beads), wax or oils. Another access means is to provide an opening or aperture, such as a slotted area on top of the helmet. If the figure is a baseball player, then the face or cap may be removable to insert the scenting/deodorizing means, or again the aperture on top of the cap would work.

The device is attached by any of a variety of known means in the art, such as a clip, to the a ventilation grill, such as those on the dashboard of a motor vehicle. For example, this can be done with an attachment to the back body portion of the device using a clip or spring wire or other attachment means, that maintains the back of the sports figure aligned in a generally vertical face to face parallel relationship with the grill face of the vehicle ventilation system. When the ventilation fan is turned on, the device is close enough to the ventilation grill face to capture the air flow, and the arms of the caricature are pinned near the shoulder area in a central location with rotating bearing means so as to rotate freely. Rotating bearing means may be concentric sleeves at the arm pivot point. The anns are typically thin but may be angled slightly or cupped at a portion thereof to capture the flow of air and to activate the rotation for mimicking a forward throwing action or in a reverse pattern to mimic an underhand throwing action, such as by a softball pitcher.

The arms therein are designed to capture air and rotate like two opposite fan blades. Alternatively, multiple arms may be added such as four arms 90 degrees apart or six arms 60 degrees apart, to mimic a continual rapid rotation of the multiple arms.

When used in an automobile, it is anticipated that children in the vehicle will be fascinated by the sports figure arms rotating and at the same time, the air in the vehicle personnel compartment can be refreshed and/or deodorized.

Figure 7:
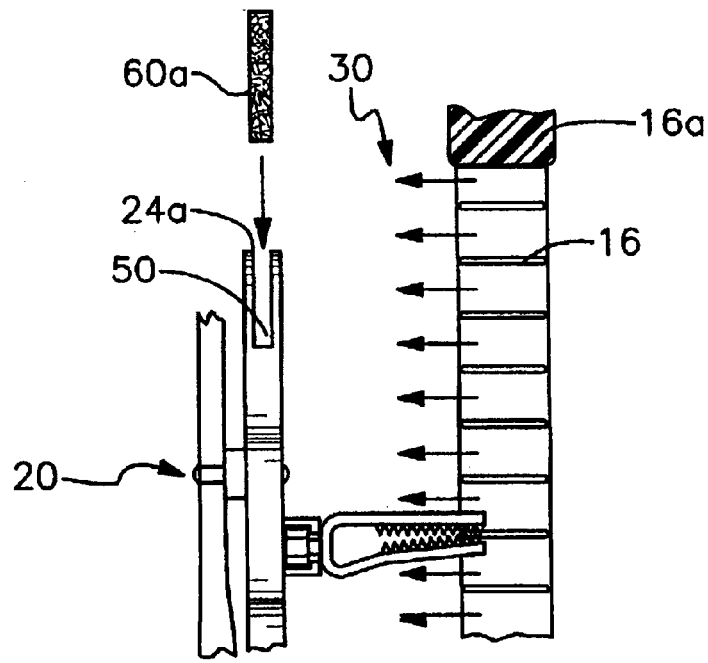
FIG. 7 is a schematic depiction of another embodiment of the invention depicting the invention connected to a grill and a slotted aperture for insertion of a cotton pad in the reservoir, wherein the cotton or otherwise absorbent pad can be saturated with a fragrance oil as depicted in FIG. 8.
Figure 8:
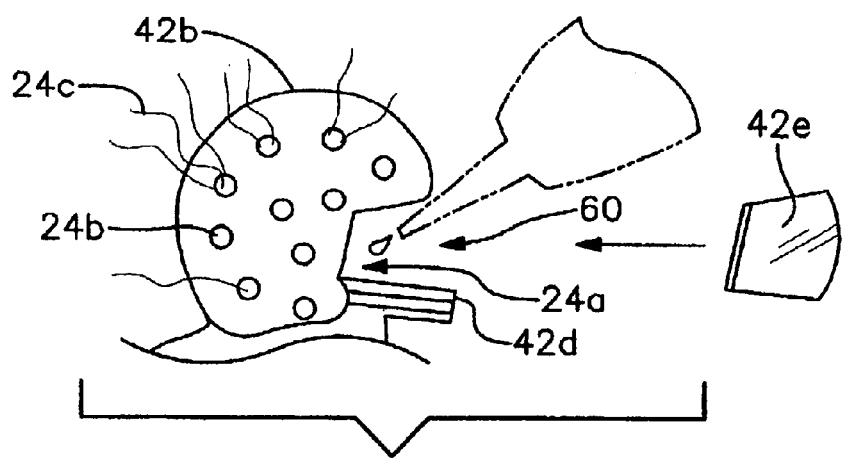
Figure 9:
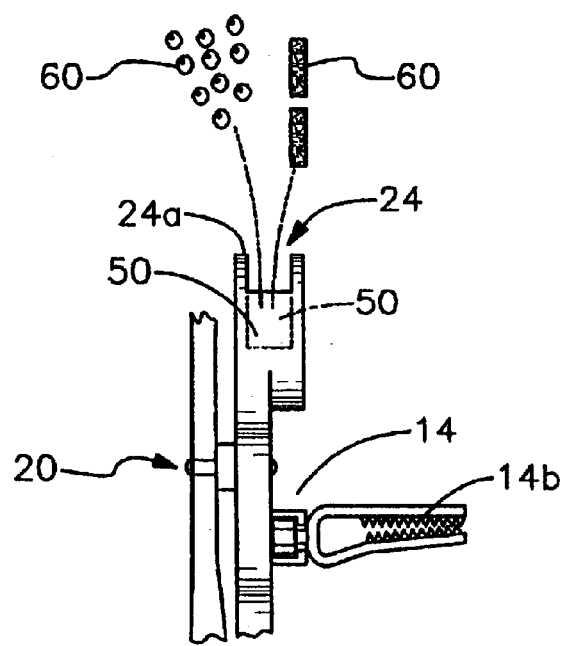

FIG. 8 is a schematic depiction of another way of accessing a reservoir for the freshener/deodorizing agents/ such as beads and wax, further specifically providing for an example, the insertion of oil drops into an absorbent pad as depicted in FIG. 7; and FIG. 9 is a schematic depiction of the alternative insertion of agents in the form of beads, granulars or blocks, in this example, through a slotted aperture at the top of the head of the caricature.

Figure 1:
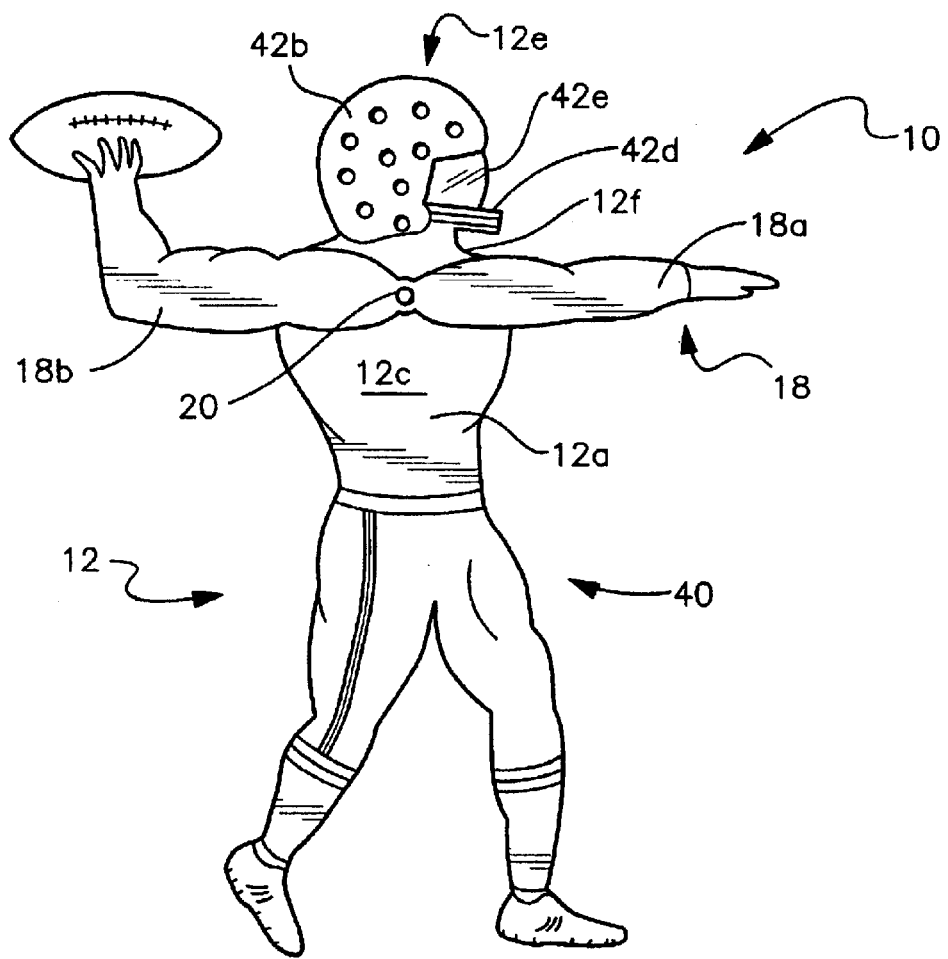
FIG. 1 is a schematic depiction of one embodiment of the invention wherein a sports figure caricature representative of a football player throwing a football is shown.

Referring now to the drawings, FIG. 1 discloses one embodiment of the present invention, which is depicted generally as 10. The invention is a sports figure shaped fan 10 for ventilation grills, such as grills 16 in dashboards 16*a* of motor vehicles. The invention 10 comprises a caricature 12 formed in the shape of a sports figure. The caricature 12 includes a central body portion 12*a* with a back side 12*b* and a front side 12*c*, two legs 12*d* depending from a lower portion of the central body 12*a* and a head and neck portion, 12*e*, 12*f* respectively, extending from an upper portion of the central body portion 12*a*.

Figure 4:
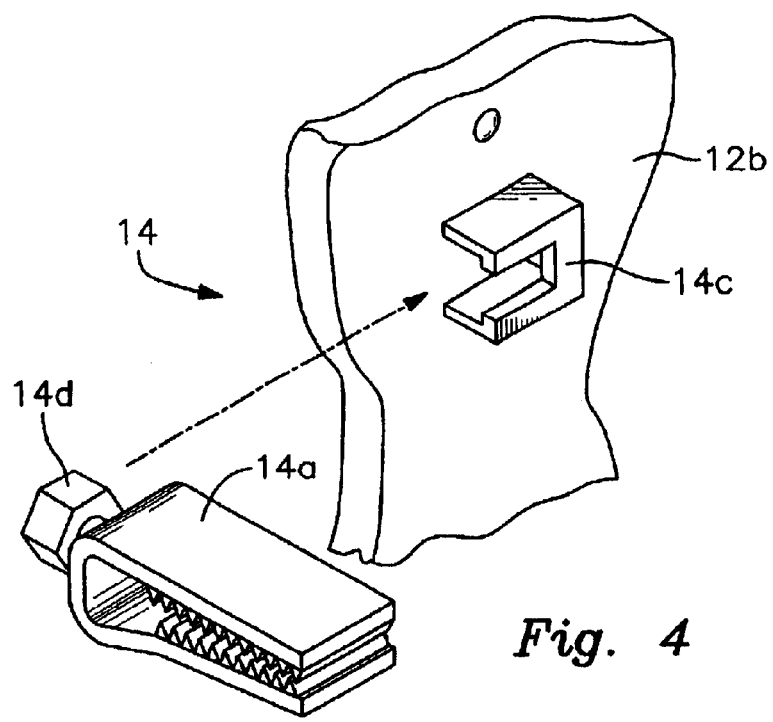
FIG. 4 is a partial exploded view taken from FIG. 2 of one embodiment of the means for attaching the caricature to the ventilation grill.

The invention 10 further includes means 14 for attaching the back side 12*b* of the central body portion 12*a* to a ventilation grill 16. The device can in fact be attached to any fan grill system, and is not limited to installation in a vehicle grill 16. FIG. 4 merely provides for one example of a preferred way of attaching the invention 10 to the grill 16. There are numerous other methods known in the art such as spring wire with bent ends, hooks, etc., that could be incorporated into the design depending on cost, practicality and preferences.

As shown in FIGS. 1–3 and 5–6, the caricature 12 further includes two arms 18, each generally extending in opposite directions from each other, the two arms 18 representing respectively a left arm 18*a* and a right arm 18*b*. The two arms 18 have means 20 for rotating about an axis of rotation at the upper portion of the central body portion 12*a*.

Figure 2:
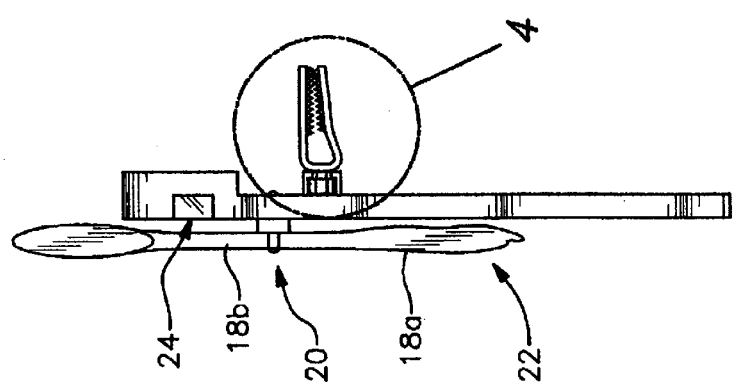
FIG. 2 is a side view of the FIG. 1 embodiment, further depicting the arms being bent or shaped at an angle to capture the air.
Figure 5:
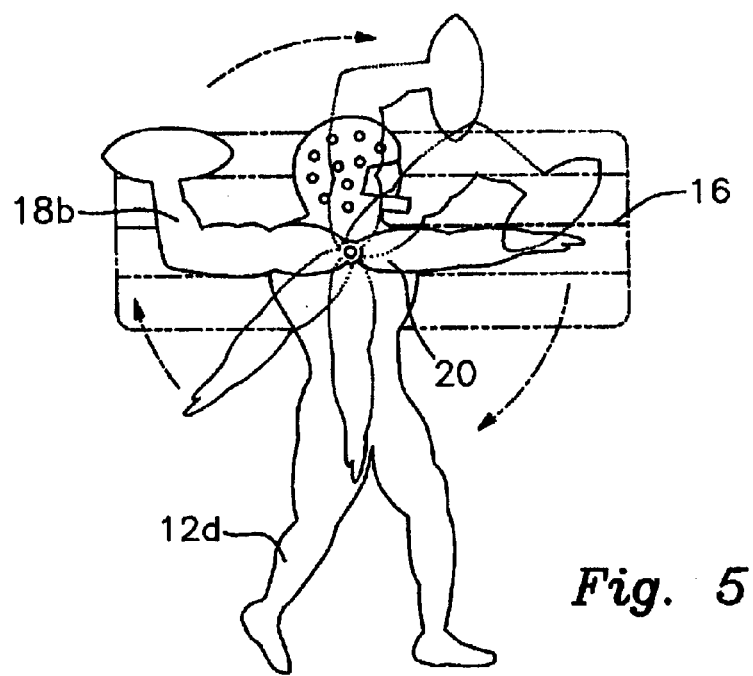
FIG. 5 is a frontal schematic depiction of the invention attached to a ventilation grill shown in phantom, with the arms rotating in an over-hand clock-wise direction.
Figure 6:
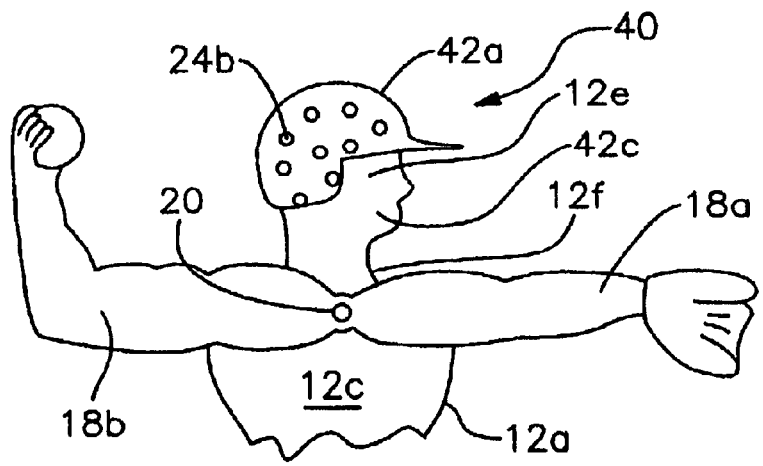
FIG. 6 is a schematic partial depiction of the invention representative of a baseball player throwing a baseball with one hand and holding a baseball glove with the other extended hand and arm.

The two arms 18 also have means 22 for capturing an air flow generated by activating a ventilation system, such as in a motor vehicle, so that air flows in a direction emanating from behind the sports figure, for creating a fanning rotation of the two arms 18, as shown by the arrows in FIG. 5, about the upper portion of the central body portion 12a in a direction mimicking a throwing action of the sports figure. The air flow emanating from a grill 16 in a dashboard 16a of an automobile is generally depicted by the arrows 30 shown in FIG. 7. FIG. 2 is a side view of the invention 10, wherein some depth to the arms in depicted with shadelines to represent bent or angularly oriented arms 18. This can be accomplished by having a slight curvature to each arm (typically along one edge) or having the arm angled in such a way that the arms, which act as fan blades, capture the air and initiate rotation. One skilled in the art need only look at any fan blade and note that there needs to be some angle or curvature to capture and/or push the air.

Figure 3:
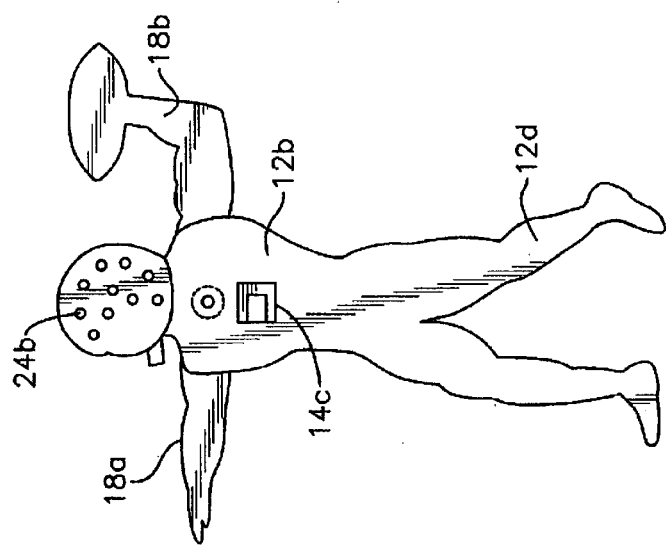
FIG. 3 is a back side view of the FIG. 1 embodiment.

At least a portion of the sports figure includes a representation of a sporting uniform 40 worn by such sports figure. For example, the caricature 12 may include representational football shoes, football pants, a football shirt and a football helmet painted or otherwise depicted on the respective feet, legs, central body portion and head of the caricature. In this representation, the depicted player may be representationally throwing a football being held in one hand. In FIGS. 1, 3 and 5, as an example, the player is depicted as a right hander throwing the football, but the sports figure could optionally be designed to be a left hander throwing the football. If the sports figure is a baseball player as partially depicted in FIG. 6, the uniform 40 would be a typical baseball uniform, including the shoes, with a baseball cap, and the hand would be holding a baseball with the fan motion depicting a pitcher throwing the ball. If the sports figure is a basketball player, then the ball may be a basketball and the uniform would be shirt and shorts and sneakers, typically worn by basketball players. In most cases, the throwing action would be simulated as an overhand throwing action. However, if a softball player is depicted, then the throwing action may be underhand, or counterclockwise rotation for a right handed pitcher.

The invention 10 further includes access means 24 for inserting one of a scenting agent, a deodorizing agent and a combination thereof, in an interior reservoir 50 in a designated portion of the caricature 12. The agents are generally represented in the drawings as 60 and may be in the form of beads or pellets, including wax (such as blocks, beads or pellets of wax), or in the form of oil absorbed or impregnated in an absorbent pad 60a such as a cotton pad. For example, FIG. 8 depicts an oil drop replenishing the reservoir (not shown in FIG. 8) containing a cotton pad 60a depicted in FIG. 7. The reservoir 50 serves as holding means for storing one of the scenting agent, the deodorizing agent and the combination thereof FIG. 9 schematically depicts the placement of agents in the form of beads (or granulars, such as pellets) or block forms entering through the slotted aperture 24a from the top into the reservoir 50. The scenting agent and/or the deodorizing agent (60) provide means for air freshening and/or deodorizing an interior compartment of the motor vehicle.

The designated portion of the caricature 12 is sufficiently permeable on either side of the interior reservoir 50, as generally depicted by perforations 24b, so that when the air flow passes by the sports figure, a vapor 24c from the scenting/deodorizing agent 60 as depicted in FIG. 8, is dispersed by the movement of the air flow 30 emanating from the ventilation grill 16.

In one embodiment, the access means 24 for inserting scenting/deodorizing agents 60 in the reservoir 50, is an aperture 24a in the designated portion of the caricature 12. Although the reservoir 50 and its access means 24 could be located on any part of the caricature 12, it is preferred that the designated portion be the head portion 12e of the caricature 12. Typically, the reservoir 50 will cause the caricature 12 to have a depth or extended portion that is designed to be in a non-interfering relationship with the rotating arms. The upper head portion lends itself to be a good selection to incorporate the reservoir 50. Where an aperture 24a is desired, the aperture can be located in the head portion 12e of the caricature 12, preferably the top.

As can be surmised, depending on the sports figure illustrated in the caricature 12, the head portion 12e may include a cap 42a (for example, for a baseball player), a helmet 42b (for example, for a football player), a face only 42c (for example, for a basketball player), a face guard 42d (for example, similar to those incorporated in football helmets), and a face visor 42e (for example, similar to those worn in combination with the face guard of a football helmet) and any combination thereof. For example, the football player may have a depicted helmet and face guard only, therefore, a part of the face would typically be depicted. A baseball player may have a baseball cap and sunglasses or a face visor to imitate drop down sunglasses from the bill of a ball cap.

An another alternative access means 24 for inserting scenting/deodorizing agents 60 in the reservoir 50 when the reservoir 50 is located in the head portion 12e, is to make a specific portion of the head portion 12e temporarily removable, such as the visor 42e shown separated from the helmet 42b in FIG. 8. In this case, the head portion 12e should be sufficiently permeable (24b) on either side of the interior reservoir 50 so that when the air flow 30 passes by the sports figure, a vapor 24c from the scenting/deodorizing agent 60 is dispersed by the movement of the air flow emanating from the ventilation grill 16.

The permeable feature can be one of more apertures 24b, including a single aperture 24b when an oil absorbent is used, or a plurality of finer apertures 24b when solid beads or waxes are used as agents 60.

While the preferred embodiment includes typically just one set of arms 18, that is, a left arm 18a and a right arm 18b, two sets or three sets of arms 18, equally angularly spaced-apart, are also contemplated. If two additional arms are included, they also generally extend in opposite directions from each other, and have means 20 for rotating about the axis of rotation at the upper portion of the central body portion 12a about which the first two arms rotate. In this embodiment, each of the arms 18 would be spaced approximately 90 degrees from each other.

FIG. 5 schematically depicts two arms in a generally 9 o'clock to 3 o'clock position and the subsequent anticipated relative rotational positions of the rotating arms are shown in phantom, one position being approximately 12 o'clock to 6 o'clock position and the intermediate position. If two additional arms were included, then the 12 o'clock to 6 o'clock position would typically be the position of the additional arms in relation to the first two, that is about 90 degrees apart and the arms would be shown in solid lines. If four additional arms were included, then the three sets of arms would be shown in solid lines and all the adjacent arms would be about 60 degrees apart (not the 45 degrees apart shown for the phantom arms depicted in FIG. 5). The embodiment with additional arms would typically be shown in solid lines but are not so depicted, as this embodiment is readily ascertainable from the schematic representation of FIG. 5.

Regarding the embodiment with two additional arms, as described above, the two additional arms 18 also include means 22 for capturing an air flow 30 generated by activating the ventilation system from behind the sports figure, for creating the fanning rotation of the arms 18 about the upper portion of the central body portion 12a in the direction mimicking the throwing action of the sports figure.

As mentioned above, in a still additional embodiment, the sports figure shaped fan 10 can include a total of six arms 18 or three sets of left and right arms 18a, 18b. In this embodiment, the arms 18 are typically spaced-apart at about a 60 degree angle from each other and all have means 20 for rotating about the axis of rotation at the upper portion of the central body portion 12a about which the arms rotate.

No matter how many sets of arms 18 are included in the invention 10, all of the arms 18 include means 22 for capturing an air flow 30 generated by activating the ventilation system from behind the sports figure, for creating the fanning rotation of the arms 18 about the upper portion of the central body portion 12a in the direction mimicking the throwing action of the sports figure.

The means 20 for rotating about an axis of rotation at the upper portion of the central body portion 12c can be provided in a number of ways known in the art. Typically and as conceptually depicted in FIGS. 2 and 3, a rotatable pin could be fixed to the arms at a central location and inserted through a tubular shaped bushing extending through the central body portion 12c. A concentric bushing acting as a spacer between the arms 18 and central body portion 12c would also typically be provided; and the pin, acting as an axis of rotation, can be designed with sufficient tolerance to rotate with relative ease when subjected to the back draft of the air flow. The end of the pin extending to the back side of the central body portion 12c could be somewhat enlarged to prevent the pin from falling out of the central body portion aperture through which the pin is inserted.

The central body portion 12a, the head and neck portion 12e, 12f respectively, the legs 12d and the arms 18 may be made from a variety of lightweight materials. For example, polymeric material or plastic based material may be used, cardboard stock material may be used, lightweight metallic material may be used and a combination of any of these materials may be used. Typically, the caricature 12 may only be about 1/16" to 3/16" thick, with the designated portion holding the reservoir 50 being about 5/32" to 3/8" in thickness. Although other thicknesses are contemplated, the emphasis in the final design is to have relatively thin arms that can freely rotate to mimic the throwing action of the sports figure. Therefore, the arms 18 acting as fan blades may typically be only about 3/64"–3/32" thick.

On example of the means 14 for attaching the back side of the central body portion 12c to the ventilation grill 16 is shown in more detail in FIG. 4. A clip 14a has a gripping portion 14b at one end thereof for gripping a portion of the ventilation grill 16 and a slotted engagement portion 14c on the back side 12b of the central body portion 12c for engaging a mating engagement pin 14d protruding from the clip 14a opposite the gripping portion 14b of the clip 14a. Engagement pin 14d is shown with its end that inserts into the slotted engagement portion 14c, shaped as a hex end. Any flat sided shape on at least two opposite sides would suffice to slide into the slotted engagement portion 14c. The slotted engagement portion is typically integral or fixed to the back side 12b of the central body portion 12c It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

Now that the invention has been described,

What is claimed is:

1. A sports figure shaped fan for ventilation grills comprising:

a caricature formed in the shape of a sports figure, the caricature including a central body portion with a front side and a back side and a head and neck portion extending from an upper portion of the central body portion;

means for attaching the back side of the central body portion to a ventilation grill;

the caricature further including two arms, each generally extending in opposite directions from each other, the two arms representing respectively a left arm and a right arm;

the two arms having means for rotating about an axis of rotation at the upper portion of the central body portion; and the two arms having means for capturing an air flow generated by activating a ventilation system so as to create an air flow emanating from behind the sports figure, and for creating a fanning rotation of the two arms about the upper portion of the central body portion in a direction mimicking a throwing action of the sports figure, wherein at least a portion of the sports figure includes a representation of a sporting uniform worn by said sports figure.

2. The sports figure shaped fan according to claim 1, further comprising:

access means for inserting one of a scenting agent, a deodorizing agent and a combination thereof, in an interior reservoir in a designated portion of the caricature;

the reservoir being holding means for storing one of the scenting agent, the deodorizing agent and the combination thereof;

said one of the scenting agent, the deodorizing agent and the combination thereof providing means for one of air freshening, deordorizing and the combination of air freshening and deodorizing; and the designated portion of the caricature being sufficiently permeable on either side of the interior reservoir so that when air flow passes by the sports figure, a vapor from said one of the scenting agent, the deodorizing agent and the combination thereof, is dispersed by the movement of the air flow emanating from the ventilation grill.

3. The sports figure shaped fan according to claim 2, wherein the access means for inserting one of the freshener scenting agent, the deodorizing agent and the combination thereof in the reservoir, is an aperture in the designated portion of the caricature.

4. The sports figure shaped fan according to claim 3, wherein the aperture is located in the head portion of the caricature.

5. The sports figure shaped fan according to claim 1, wherein the head portion includes one of a cap, a helmet, a face, a face guard, a face visor and a combination thereof.

6. The sports figure shaped fan according to claim 5,
wherein a pre-determined portion of the head portion is temporarily removable to provide access to an interior reservoir serving as holding means for storing one of a scenting agent, a deodorizing agent and a combination thereof;

said one of the scenting agent, the deodorizing agent and the combination thereof providing means for one of air freshening, deodorizing and the combination of air freshening and deodorizing; and the head portion being sufficiently permeable on either side of the interior reservoir so that when the air flow passes by the sports figure, a vapor from said one of the scenting agent, the deodorizing agent and the combination thereof, is dispersed by the movement of the air flow emanating from the ventilation grill.

7. The sports figure shaped fan according to claim 1, further comprising:

two additional arms, each generally extending in opposite directions from each other, the two additional arms respectively representing a left arm and a right arm, the two additional arms having means for rotating about the axis of rotation at the upper portion of the central body portion about which the two arms rotate.

8. The sports figure shaped fan according to claim 7,
wherein the two additional arms are approximately 90 degrees from each of the respective left and right arms of the two arms.

9. The sports figure shaped fan according to claim 7,
wherein the two additional arms include means for capturing an air flow generated by activating the ventilation system ventilation system so as to create an air flow eminating from behind the sports figure, for creating the fanning rotation of the two arms and two additional arms about the upper portion of the central body portion in the direction mimicking the throwing action of the sports figure.

10. The sports figure shaped fan according to claim 1, further comprising:

four additional arms, each generally extending in opposite directions from each other and each set of the four additional arms representing respective left and right arms, the four additional arms having means for rotating about the axis of rotation at the upper portion of the central body portion about which the two arms rotate.

11. The sports figure shaped fan according to claim 10,
wherein the four additional arms, in combination with the two arms, are each approximately 60 degrees from each adjacent arm.

12. The sports figure shaped fan according to claim 10,
wherein the four additional arms include means for capturing an air flow generated by activating the ventilation system ventilation system so as to create an air flow emanating from behind the sports figure, for creating the fanning rotation of the two arms and four additional arms about the upper portion of the central body portion in the direction mimicking the throwing action of the sports figure.

13. The sports figure shaped fan according to claim 1, wherein the central body portion, the head and neck portion, the legs and two arms are made from material selected from the group comprising one of polymeric material, cardboard material, light-weight metallic material and a combination thereof.

14. The sports figure shaped fan according to claim 1, wherein the means for attaching the back side of the central body portion to the ventilation grill comprises: a clip having a gripping portion at one end thereof for gripping a portion of the ventilation grill and a slotted engagement portion on the back side of the central body portion for engaging a mating engagement pin protruding from the clip opposite the gripping portion of the clip.

* * * * *